United States Patent
Wooh et al.

(10) Patent No.: US 6,382,028 B1
(45) Date of Patent: May 7, 2002

(54) ULTRASONIC DEFECT DETECTION SYSTEM

(75) Inventors: Shi-Chang Wooh, Bedford; Ji-Yong Wang, Malden, both of MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/654,673

(22) Filed: Sep. 5, 2000

Related U.S. Application Data
(60) Provisional application No. 60/184,496, filed on Feb. 23, 2000.

(51) Int. Cl.[7] .................................................. G01N 9/24
(52) U.S. Cl. .............................. 73/602; 73/620; 73/628
(58) Field of Search ........................... 73/570, 596, 600, 73/602, 606, 615, 619, 620, 625, 627, 1.82, 599, 618, 628, 624; 356/432, 450

(56) References Cited

U.S. PATENT DOCUMENTS

| | | | |
|---|---|---|---|
| 4,497,210 A | * | 2/1985 | Uchida et al. ................. 73/602 |
| 6,092,420 A | * | 7/2000 | Kimura et al. ................. 73/620 |
| 6,128,092 A | * | 10/2000 | Levesque et al. ........... 356/432 |

* cited by examiner

*Primary Examiner*—Hezron Williams
*Assistant Examiner*—Jacques Saint-Surin
(74) *Attorney, Agent, or Firm*—Iandiorio & Teska

(57) ABSTRACT

An ultrasonic defect detection system includes a steered beam transmitter for directing an ultrasonic beam through the front face to the back face of a specimen; a sensor device for sensing the location on the front face of the near shadow of a defect from the beam reflected from the back face before the defect and the far shadow of the defect from the beam reflected from the back face after the defect; and an arithmetic circuit responsive to the location of the shadows on the front face for determining the distance between the transmitter and the near and far boundary of the near shadow and at least the near boundary of the far shadow for calculating the location and/or the size and/or the orientation of the defect.

19 Claims, 3 Drawing Sheets

ULTRASONIC DEFECT DETECTION SYSTEM

RELATED APPLICATIONS

This application claims benefit of U.S. Provisional Application No. 60/184,496 filed on Feb. 23, 2000 and entitled A MULT-ELEMENT ULTRASONIC ARRAY TRANSDUCER AND METHOD FOR DETECTING AND MEASURING THE SIZE AND LOCATION OF TRANSVERSE DEFECTS IN THICK PLATES, BARS, AND LAYERED MEDIA.

FIELD OF THE INVENTION

This invention relates to an ultrasonic defect detection system, and more particularly to such a system which can detect location and/or size and/or orientation of a defect.

BACKGROUND OF THE INVENTION

It is often desirable to know not just when a defect is located in a specimen such as a rail but also its size. Presently, the so called delta technique is used for this purpose. The delta technique slides an ultrasonic transmitter/receiver transducer along the front face of the rail directing a beam onto the rail at a fixed known angle for example 45°. Assuming the defect is transversely or vertically oriented the weak diffraction from the tips of the defect define a distance on the face of the rail. Using this distance and basic geometry, the size or height of the defect can be determined. However, this only applies when the defect is transverse or vertical. If it is not transverse or vertical, its orientation is unknown and its height or length or size will be indeterminate.

BRIEF SUMMARY OF THE INVENTION

It is therefore an object of this invention to provide an improved ultrasonic defect detection system.

It is a further object of this invention to provide such an improved ultrasonic defect detection system which can determine any one or more of the location, size and orientation of a defect.

It is a further object of this invention to provide such an improved ultrasonic defect detection system which is effective regardless of the orientation of the defect.

It is a further object of this invention to provide such an improved ultrasonic defect detection system which does not require mechanical scanning.

It is a further object of this invention to provide such an improved ultrasonic defect detection system which can cover large inspection areas.

It is a further object of this invention to provide such an improved ultrasonic defect detection system which requires access to only one side of a specimen.

It is a further object of this invention to provide such an improved ultrasonic defect detection system which can be used automatically without a highly skilled operator.

The invention results from the realization that a truly simple and more effective ultrasonic defect detection system capable of determining any one or more of the location, size and orientation of a defect can be achieved with steered beam reflected off the back face of a specimen to create on the front face near and far shadows bracketing the defect and using the position of boundaries of those shadows to calculate location, size and orientation.

This invention features an ultrasonic defect detection system including a steered beam transmitter for directing an ultrasonic beam through the front face to the back face of a specimen. There is a sensor device for sensing the location on the front face of the near shadow of a defect from the beam reflected from the back face before the defect and the far shadow of the defect from the beam reflected from the back face after the defect. An arithmetic circuit responsive to the location of the shadows on the front face determines the distance between the transmitter and the near and far boundary of the near shadow and at least the near boundary of the far shadow for calculating the location of the defect.

In a preferred embodiment the arithmetic circuit may also calculate the size of the defect and may also calculate the orientation of the defect. The transmitter may include an ultrasonic phased array transducer. The transmitter may include a variable angle ultrasonic wedge transducer. The sensor device may include an interferometer. It may be a laser interferometer. The sensor device may include a piezoelectric receiver array. The arithmetic circuit may include a microprocessor. The arithmetic circuit may calculate the location of the defect using the expressions:

$$x_0 = \frac{1}{2}\left(\frac{x_A x_D}{x_A + x_D} + \frac{x_B x_C}{x_B + x_C}\right)$$

$$y_0 = L\left(\frac{x_A}{x_A + x_D} + \frac{x_B}{x_B + x_C}\right)$$

The invention also features an ultrasonic defect detection system including a steered beam transmitter for directing an ultrasonic beam through the front face to the back face of a specimen. A sensor device senses the location on the front face of the near shadow of a defect from the beam reflected from the back face before the defect and the far shadow of the defect from the beam reflected from the back face after the defect. An arithmetic circuit responsive to the location of the shadows on the front face determines the distance between the transmitter and the near and far boundary of the near shadow and at least the near boundary of the far shadow for calculating the size of the defect.

In a preferred embodiment the arithmetic circuit may calculate the location of the defect and may calculate the orientation of the defect. The arithmetic circuit may calculate the size of the defect using the expression:

$$b = \sqrt{\frac{x_A^2(4L^2 + x_D^2)}{(x_A + x_D)^2} + 2x_A x_B \frac{4L^2 - x_C x_D}{(x_A + x_D)(x_B + x_C)} + \frac{x_B^2(4L^2 + x_C^2)}{(x_B + x_C)^2}}$$

The invention also features an ultrasonic defect detection system including a steered beam transmitter for directing an ultrasonic beam through the front face to the back face of a specimen. A sensor device senses the location on the front face of the near shadow of a defect from the beam reflected from the back face before the defect and the far shadow of the defect from the beam reflected from the back face after the defect. An arithmetic circuit responsive to the location of the shadows on the front face determines the distance between the transmitter and the near and far boundary of the near shadow and at least the near boundary of the far shadow for calculating the orientation of the defect.

In a preferred embodiment the arithmetic circuit may also calculate the location of the defect; the arithmetic circuit may also calculate the size of the defect. The arithmetic circuit may calculate the orientation of the defect using the expression:

$$\phi = \tan^{-1}\left(\frac{x_A x_B (x_C - x_D) - (x_A - x_B) x_C x_D}{2L(x_B x_D - x_A x_C)}\right)$$

The invention also features an ultrasonic defect detection system including a steered beam transmitter for directing an ultrasonic beam through the front face to the back face of a specimen. A sensor device senses the location on the front face of the near shadow of a defect from the beam reflected from the back face before the defect and the far shadow of the defect from the beam reflected from the back face after the defect. An arithmetic circuit responsive to the location of the shadows on the front face determines the distance between the transmitter and the near and far boundary of the near shadow and at least the near boundary of the far shadow for calculating the location, size and orientation of the defect.

BRIEF DESCRIPTION OF THE DRAWINGS

Other objects, features and advantages will occur to those skilled in the art from the following description of a preferred embodiment and the accompanying drawings, in which.

PREFERRED EMBODIMENT

Figure 1:
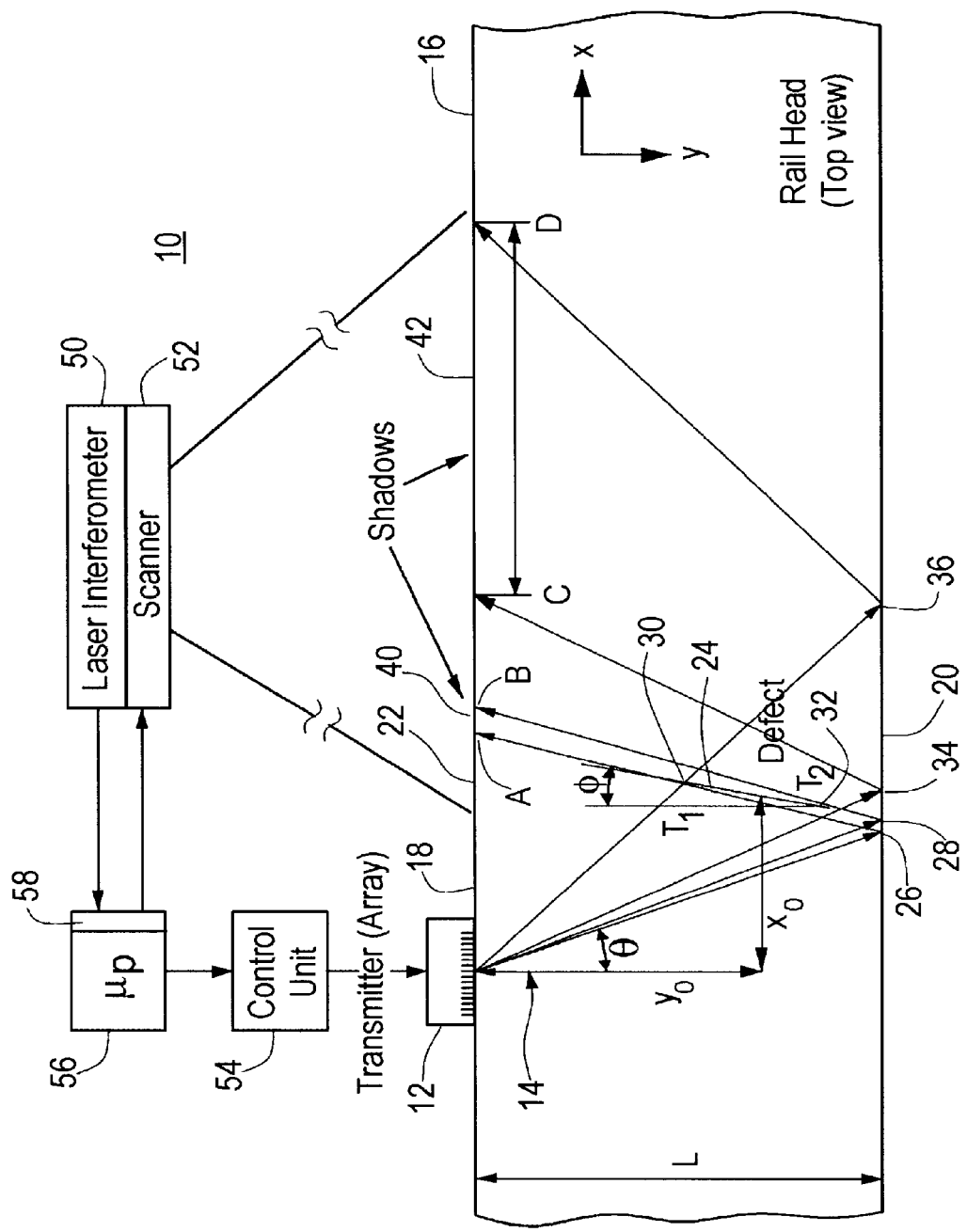
FIG. 1 is a schematic diagram of an ultrasonic defect detection system according to this invention.

There is shown in FIG. 1 an ultrasonic defect detection system 10 according to this invention including a steering transducer 12 such as a phased array which sweeps an ultrasonic beam 14 through a range of angles θ from the Y-axis. The beam 14 is directed into the specimen 16 such as a rail to be examined. The beam enters the front face 18 and reflects off the back face 20 to return again to the front face 22. Assuming a defect 24 exists at a slight angle as shown, this system is capable of determining not only that the defect exists and its location, but also its size and orientation.

As phased array 12 sweeps beam 14 through angle θ, the beam first strikes back face 20 in front of defect 24 at point 26 and then later at point 28. When the beam strikes point 26 and is reflected up, it just misses the top corner 30 of defect 24. When beam 14 reflects off point 28 it just misses the lower edge 32 of defect 24. Those two beams strike front face 22 at points A and B. Between those two points defect 24 causes a shadow of ultrasonic energy whereas to the left of A and to the right of B there is no shadow because the defect does not interrupt the reflected waves. Similarly, as beam 14 continues to sweep through angle θ it strikes back face 20 at points 34 and 36 creating a second shadow between points C and D. The shadow between points A and B is referred to as a near shadow 40 while the shadow between points C and D is referred to as far shadow 42. These shadows, actually areas of low ultrasonic energy as opposed to the interstitial areas where there is high ultrasonic energy, define boundaries A, B, C and D from which the location, size and even orientation of the flow can be determined. The presence and location of the boundaries are sensed by a laser interferometer 50 in conjunction with scanner 52 that scans the laser beam across the front face 18 of rail 16. Control unit 54 controls the scanning of phased array 12 through the angle θ. Microprocessor 56 synchronizes the operation of the laser scanner 52 and the phased array 12 so that scanner 52 is looking at the spot on front face 18 that is presently receiving the reflected beam 14.

Figure 2:
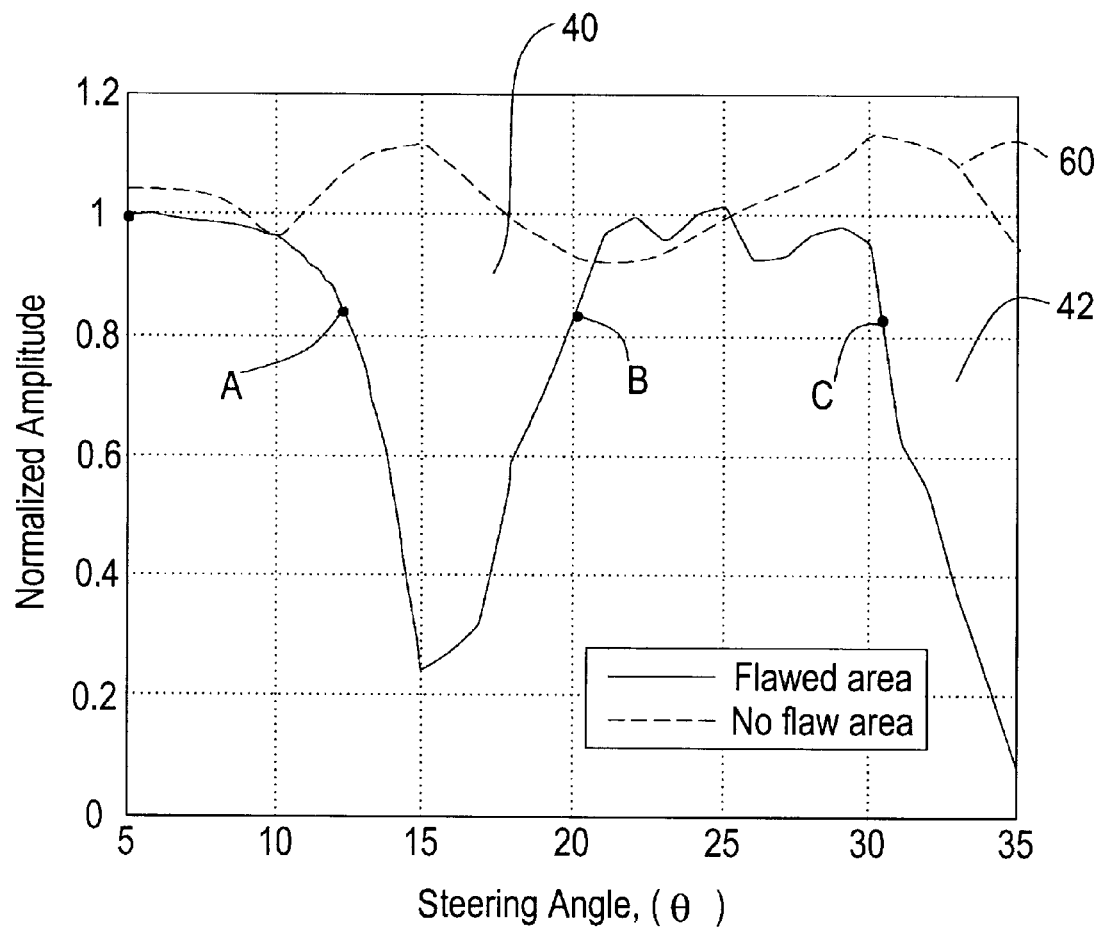
FIG. 2 is an illustration of the amplitude variation of the near and far shadows with and without flaws created by the system of FIG. 1.

Once the near 40 and far 42 shadows have been sensed by interferometer 50 they are provided to an arithmetic circuit 58 which can be a separate component or a part of microprocessor 56 and the location, size and orientation of the defect can be determined in accordance with the following equations:

$$\text{(location)} \quad x_0 = \frac{1}{2}\left(\frac{x_A x_D}{x_A + x_D} + \frac{x_B x_C}{x_B + x_C}\right) \quad (1)$$

$$\text{(location)} \quad y_0 = L\left(\frac{x_A}{x_A + x_D} + \frac{x_B}{x_B + x_C}\right) \quad (2)$$

$$\text{(orientation)} \quad \phi = \tan^{-1}\left(\frac{x_A x_B (x_C - x_D) - (x_A - x_B) x_C x_D}{2L(x_B x_D - x_A x_C)}\right) \quad (3)$$

$$\text{(size)} \quad b = \quad (4)$$

$$\sqrt{\frac{x_A^2 (4L^2 + x_D^2)}{(x_A + x_D)^2} + 2 x_A x_B \frac{4L^2 - x_C x_D}{(x_A + x_D)(x_B + x_C)} + \frac{x_B^2 (4L^2 + x_C^2)}{(x_B + x_C)^2}}$$

where location can be determined from the x and y coordinates, $x_0$, $y_0$ of equations (1) and (2), the orientation from equation (3), and the size from equation (4). The distances $x_A$, $x_B$, $x_C$, $x_D$ are the distances between the center of the transmitter and the points A, B, C and D on face 18. Distance L is the width of the specimen and $\phi$ is the orientation of the defect as depicted in FIG. 1. The robustness of the shadow's representation on the face 18 can be seen in FIG. 2 where the normal profile 60 shown in dashed lines which occurs when there is no defect present maintains a fairly flat profile whereas in contrast when a flaw is present, as represented by the solid line, there is a pronounced dip at near shadow 40 and far shadow 42 in between the points A and B, and C and D, respectively (D not shown). Often in the operation of the system the other end of far shadow 42, point D, is too far to be accommodated by the system. In that case, the location and size of the flaw can still be detected if the crack is oriented in the transverse direction (which is the common situation for many instances). The location and size can be determined from the following equations:

$$b = 2L\frac{(x_B - x_A)x_C}{x_A(x_B + x_C)} \quad (5)$$

$$x_0 = \frac{x_B x_C}{x_B + x_C} \quad (6)$$

$$y_0 = L\left(1 + \frac{x_B(x_A - x_C)}{x_A(x_B + x_C)}\right) \quad (7)$$

Figure 3:
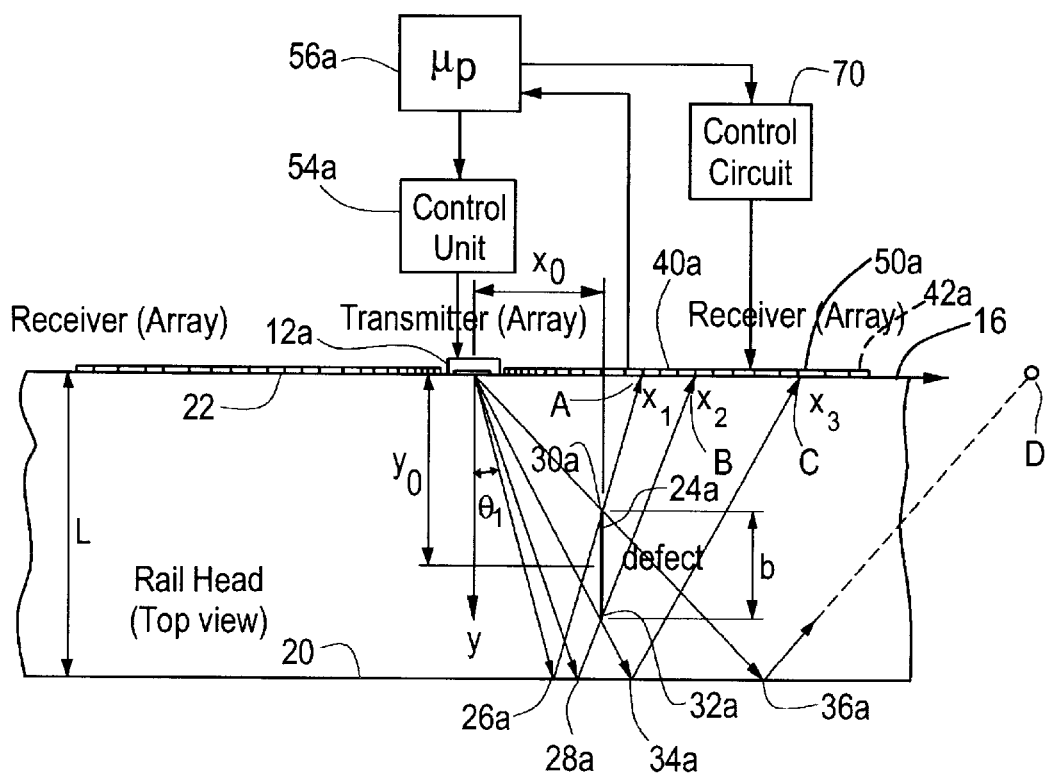
FIG. 3 is a view similar to FIG. 1 using an alternative receiver array.

Although thus far the embodiment of FIG. 1 uses a laser interferometer to sense the shadows, this is not a necessary limitation of the invention. For example, as shown in FIG. 3 the receiver 50a may instead be a piezoelectric array mounted directly on the front face 18 of rail 16. Here again microprocessor 56a or a similar device performs the calculations of equations (1), (2), (3) and (4) and synchronizes the operation of phased array 12*a* and piezoelectric receiver array 50*a* through control unit 54*a* and control circuit 60, respectively.

Figure 4:
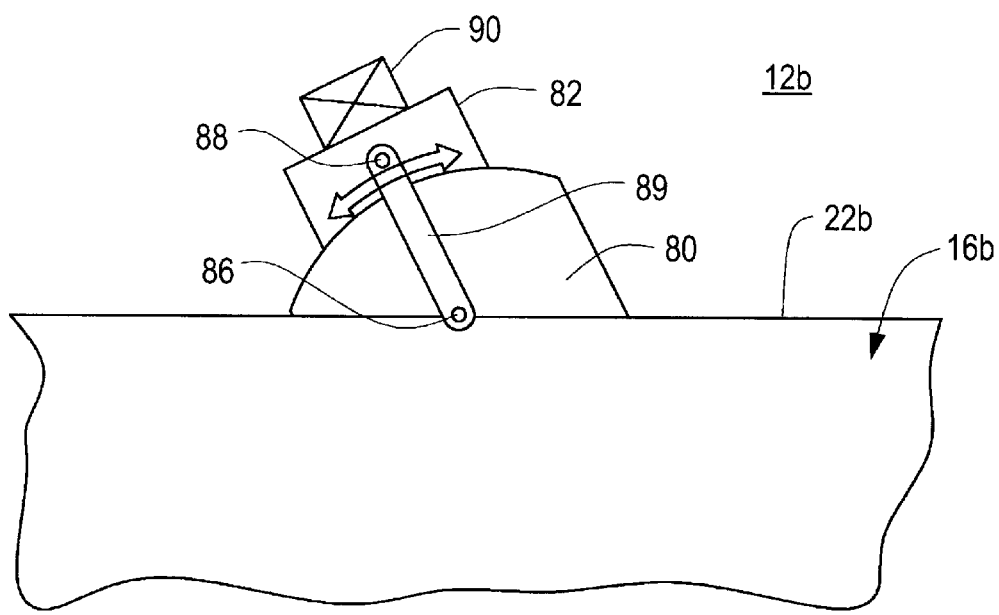
FIG. 4 is a schematic diagram of a variable angle ultrasonic wedge transducer which may be used with this invention.

Although the transmitter has thus far been shown as a phased array, this is not a necessary limitation either as any number of transmitters may be used which are capable of sweeping the beam. For example, a variable angle ultrasonic wedge transducer 12*b*, FIG. 4, employing a wedge 80 which interfaces with front face 22*b* of rail 16*b* may be employed with a movable or slidable block 82 pivotably mounted by arm 84 at pivots 86 and 88 to wedge 80. Transmitting transducer 90 is mounted on top of block 82.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. An ultrasonic defect detection system comprising:

a steered beam transmitter for directing an ultrasonic beam through the front face to the back face of a specimen;

a sensor device for sensing the location on the front face of the near shadow of a defect from the beam reflected from the back face of the specimen before the defect and the far shadow of the defect from the beam reflected from the back face after the defect; and an arithmetic circuit responsive to the location of the shadows on the front face for determining the distance between the transmitter and the near and far boundary of the near shadow and at least the near boundary of the far shadow for calculating the location of the defect.

2. The ultrasonic defect detection system of claim 1 in which said arithmetic circuit also calculates the size of the defect.

3. The ultrasonic defect detection system of claim 1 in which said arithmetic circuit also calculates the orientation of the defect.

4. The ultrasonic defect detection system of claim 1 in which said transmitter includes an ultrasonic phased array transducer.

5. The ultrasonic defect detection system of claim 1 in which said transmitter includes a variable angle ultrasonic wedge transducer.

6. The ultrasonic defect detection system of claim 1 in which said sensor device includes an interferometer.

7. The ultrasonic defect detection system of claim 6 in which said sensor device includes a laser interferometer.

8. The ultrasonic defect detection of claim 6 in which said sensor device includes a piezoelectric receiver array.

9. The ultrasonic defect detection system of claim 1 in which said arithmetic circuit includes a microprocessor.

10. The ultrasonic defect detection of claim 1 in which said arithmetic circuit calibrates the location of the defect using the expressions $$x_0 = \frac{1}{2}\left(\frac{x_A x_D}{x_A + x_D} + \frac{x_B x_C}{x_B + x_C}\right) \quad (1)$$

$$y_0 = L\left(\frac{x_A}{x_A + x_D} + \frac{x_B}{x_B + x_C}\right). \quad (2)$$

11. An ultrasonic defect detection system comprising:

a steered beam transmitter for directing an ultrasonic beam through the front face to the back face of a specimen;

a sensor device for sensing the location on the front face of the near shadow of a defect from the beam reflected from the back face of the specimen before the defect and the far shadow of the defect from the beam reflected from the back face after the defect; and an arithmetic circuit responsive to the location of the shadows on the front face for determining the distance between the transmitter and the near and far boundary of the near shadow and at least the near boundary of the far shadow for calculating the size of the defect.

12. The ultrasonic defect detection system of claim 11 in which said arithmetic circuit also calculates the location of the defect.

13. The ultrasonic defect detection system of claim 11 in which said arithmetic circuit also calculates the orientation of the defect.

14. The ultrasonic defect detection of claim 11 in which said arithmetic circuit calibrates the size of the defect using the expression:

$$b = \sqrt{\frac{x_A^2(4L^2 + x_D^2)}{(x_A + x_D)^2} + 2x_A x_B \frac{4L^2 - x_C x_D}{(x_A + x_D)(x_B + x_C)} + \frac{x_B^2(4L^2 + x_C^2)}{(x_B + x_C)^2}}.$$

15. An ultrasonic defect detection system comprising:

a steered beam transmitter for directing an ultrasonic beam through the front face to the back face of a specimen;

a sensor device for sensing the location on the front face of the near shadow of a defect from the beam reflected from the back face of the specimen before the defect and the far shadow of the defect from the beam reflected from the back face after the defect; and an arithmetic circuit responsive to the location of the shadows on the front face for determining the distance between the transmitter and the near and far boundary of the near shadow and at least the near boundary of the far shadow for calculating the orientation of the defect.

16. The ultrasonic defect detection system of claim 15 in which said arithmetic circuit also calculates the size of the defect.

17. The ultrasonic defect detection system of claim 15 in which said arithmetic circuit calculates the location of the defect.

18. The ultrasonic defect detection of claim 15 in which said arithmetic circuit calibrates the orientation of the defect using the expression:

$$\phi = \tan^{-1}\left(\frac{x_A x_B(x_C - x_D) - (x_A - x_B)x_C x_D}{2L(x_B x_D - x_A x_C)}\right).$$

19. An ultrasonic defect detection system comprising:

a steered beam transmitter for directing an ultrasonic beam through the front face to the back face of a specimen;

a sensor device for sensing the location on the front face of the near shadow of a defect from the beam reflected from the back face of the specimen before the defect and the far shadow of the defect from the beam reflected from the back face after the defect; and an arithmetic circuit responsive to the location of the shadows on the front face for determining the distance between the transmitter and the near and far boundary of the near shadow and at least the near boundary of the far shadow for calculating the location, size and orientation of the defect.

* * * * *